(12) United States Patent
Okutsu

(10) Patent No.: US 9,987,610 B2
(45) Date of Patent: Jun. 5, 2018

(54) CRYSTALLIZATION SUBSTRATE, CRYSTALLIZATION CONTAINER, CRYSTALLIZATION DEVICE, AND CRYSTAL PRODUCING METHOD

(71) Applicant: NATIONAL UNIVERSITY CORPORATION GUNMA UNIVERSITY, Maebashi-shi, Gunma (JP)

(72) Inventor: Tetsuo Okutsu, Kiryu (JP)

(73) Assignee: National University Corporation Gunma University, Maebashi-shi (JP)

(*) Notice: Subject to any disclaimer, the term of this patent is extended or adjusted under 35 U.S.C. 154(b) by 902 days.

(21) Appl. No.: 14/375,676

(22) PCT Filed: Jan. 25, 2013

(86) PCT No.: PCT/JP2013/051544
§ 371 (c)(1),
(2) Date: Jul. 30, 2014

(87) PCT Pub. No.: WO2013/115080
PCT Pub. Date: Aug. 8, 2013

(65) Prior Publication Data
US 2015/0017702 A1 Jan. 15, 2015

(30) Foreign Application Priority Data
Jan. 31, 2012 (JP) ................. 2012-018239

(51) Int. Cl.
*C30B 29/58* (2006.01)
*B01J 19/08* (2006.01)
(Continued)

(52) U.S. Cl.
CPC ............ *B01J 19/08* (2013.01); *C12N 9/2462* (2013.01); *C23C 14/18* (2013.01); *C30B 7/00* (2013.01);
(Continued)

(58) Field of Classification Search
CPC ................................ C30B 29/58; B01J 19/08
See application file for complete search history.

(56) References Cited

U.S. PATENT DOCUMENTS

2005/0158208 A1 7/2005 Mino et al.
2005/0241568 A1 11/2005 Sasaki et al.
(Continued)

FOREIGN PATENT DOCUMENTS

JP       6-116098 A     4/1994
JP       2003-95800 A   4/2003
(Continued)

OTHER PUBLICATIONS

European Patent Office, English computer translation of JP 2009-234963 (2017).*
(Continued)

*Primary Examiner* — Matthew Song
(74) *Attorney, Agent, or Firm* — Birch, Stewart, Kolasch & Birch, LLP

(57) ABSTRACT

A crystallization substrate of the present invention includes a noble metal vapor-deposited film having an absorbance in a 500 to 1,000 nm wavelength range and formed in all or part of one surface of the substrate. The noble metal vapor-deposited film has an average thickness of 0.1 to 60 nm. The noble metal vapor-deposited film is a continuous film with a pit formed by vapor deposition in part of the film and surrounded by the continuous film.

13 Claims, 8 Drawing Sheets

(51) Int. Cl.
*C30B 7/00* (2006.01)
*C12N 9/36* (2006.01)
*C23C 14/18* (2006.01)

(52) U.S. Cl.
CPC ....... *C30B 29/58* (2013.01); *B01J 2219/0879* (2013.01); *Y10T 428/24355* (2015.01)

(56) References Cited

U.S. PATENT DOCUMENTS

| | | | |
|---|---|---|---|
| 2006/0061762 A1* | 3/2006 | Dwight | B82Y 30/00 356/301 |
| 2007/0264437 A1* | 11/2007 | Zimmermann | C09D 4/00 427/445 |
| 2012/0094220 A1* | 4/2012 | Yoshiyasu | G03F 1/50 430/5 |
| 2012/0204783 A1 | 8/2012 | Okutsu et al. | |

FOREIGN PATENT DOCUMENTS

| | | | | |
|---|---|---|---|---|
| JP | 2003-306497 A | | 10/2003 | |
| JP | 2005-206454 A | | 8/2005 | |
| JP | 2007-254415 A | | 10/2007 | |
| JP | 2009-234963 A | | 10/2009 | |
| JP | 2009234963 A | * | 10/2009 | ............ C07K 17/00 |
| WO | WO 2004/018744 A1 | | 3/2004 | |
| WO | WO 2011/030704 A1 | | 3/2011 | |

OTHER PUBLICATIONS

Haruta et al., "Protein crystallization induced by strong photons-molecules coupling fields photochemical reaction", Journal of Photochemistry and Photobiology A: Chemistry, Jun. 25, 2011, vol. 221, Issues 2-3, pp. 268-272.
Hodzhaoglu et al., Gold nanoparticles induce protein crystallization, Crystal Research and Technology, 2008, vol. 43, No. 6, pp. 588-593.
International Search Report, dated Apr. 23, 2013, issued in PCT/JP2013/051544.
Ji et al., Improved protein crystallization by vapor diffusion from drops in contact with transparent, self-assembled monolayers on gold-coated glass coverslips, Journal of Crystal Growth, 2000, vol. 218, pp. 390-398.
Tsunehiro Takano "Crystallization", New Biochemical Experimental Course 1 "Protein I—Separation, Purification, Nature -" edited by The Japanese Biochemical Society, published by Tokyo Kagaku Dozin Co., Ltd., 1990, pp. 407-415.
Wang et al., Shape-Control of Protein Crystals in Patterned Microwells, Journal of the American Chemical Society, 2008, vol. 130, No. 7, pp. 2142-2143.
Extended European Search Report dated Oct. 9, 2015 for Counterpart Application No. 13743894.1.
Haruta et al., "Protein Crystallization Induced by Strong Photons-Molecules Coupling Fields Photochemical Reaction", Journal of Photochemistry and Photobiology A: Chemistry vol. 221, No. 2, 2011, (Available online Mar. 23, 2011), pp. 268-272.

* cited by examiner

CRYSTALLIZATION SUBSTRATE, CRYSTALLIZATION CONTAINER, CRYSTALLIZATION DEVICE, AND CRYSTAL PRODUCING METHOD

TECHNICAL FIELD

The present invention relates to a crystallization substrate, a crystallization container, a crystallization device, and a crystal producing method, specifically to a crystallization substrate, a crystallization container, a crystallization device, and a crystal producing method particularly preferred for use for biopolymer crystals.

BACKGROUND ART

Methods such as a batch method, a dialysis method, a liquid-liquid diffusion method, and a gas-liquid diffusion method have been used for crystallization of biopolymers such as proteins (see Non-Patent Document 1).

Taking the batch method as an example, a precipitant such as ammonium sulfate is directly added to a protein solution until a crystallization concentration is reached. Typically, the precipitant is added to the biopolymer solution in a container, and biopolymer crystals are produced by supersaturating the biopolymer under controlled conditions. The batch method, however, involves certain drawbacks, including large quantities of high-concentration polymer sample, skilled operation and poor repeatability, and difficulties in the screening of crystallization conditions. Further drawbacks of the foregoing crystallization methods are that the methods require relatively specific crystallization conditions for specific polymers, and are not usable under general conditions.

For example, Patent Document 1 discloses a technique in which a protein solution of a preset temperature condition suited for nucleation of protein crystals is irradiated with a laser beam, which is presumably a visible laser beam. The scattering of the laser beam is then analyzed to detect that the protein crystal nucleation has started, upon which the protein solution is brought to a controlled temperature condition suited for crystal growth.

Patent Document 2 discloses a method whereby a solution existing in a supersaturated state but with a low degree of supersaturation (metastable solution) unsuited for protein crystal nucleation is irradiated with the 266 nm fourth harmonic wave of a neodymium YAG laser, or with 500 W xenon lamp light to create crystals of chicken egg white lysozyme.

Patent Document 3 discloses a method for producing a crystal nucleus whereby a solution dissolving the crystallization target solute is irradiated with at least one of a picosecond pulsed laser and a femtosecond pulsed laser to generate a crystal nucleus.

Patent Document 4 discloses a biopolymer crystallization container of a structure in which two or more noble metals and/or two or more materials covered with noble metal are disposed in 1 to 1,000 nm intervals.

PRIOR ART DOCUMENTS

Patent Documents

Patent Document 1: JP-A-6-116098 (JP-A denotes a Japanese unexamined patent application publication)
Patent Document 2: JP-A-2003-306497
Patent Document 3: WO2004/018744
Patent Document 4: WO2011/030704

Non-Patent Document

Non-Patent Document 1: Shin Seikagaku Jikken Koza 1, ed., The Japanese Biochemical Society, Protein I—Separation, Purification, and Property—, 1990, Tokyo Kagaku Dojin, Tsunehiro Takano, Chapter 14, Crystallization

SUMMARY OF THE INVENTION

Problems to be Solved by the Invention

An object of the present invention is to provide a crystallization substrate, a crystallization container, a crystallization device, and a crystal producing method with which crystals, preferably biopolymer crystals can be conveniently and efficiently produced.

Means for Solving the Problems

The above-mentioned objects of the present invention have been attained by means <1>, <13>, <14>, <16>, <18>, or <20> to <22> below. They are listed together with <2> to <12>, <15>, <17>, and <19>, which are preferred embodiments.

<1> A biopolymer crystallization substrate comprising:
a noble metal vapor-deposited film having an absorbance in a 500 to 1,000 nm wavelength range and formed in all or part of one surface of the substrate,
wherein the noble metal vapor-deposited film has an average thickness of 0.1 to 60 nm, and
wherein the noble metal vapor-deposited film is a continuous film with pits formed by vapor deposition in part of the film and surrounded by the continuous film.

<2> The biopolymer crystallization substrate according to <1>, wherein the absorbance of the noble metal vapor-deposited film at 600 nm wavelength is 0.08 to 0.5, <3> the biopolymer crystallization substrate according to <1> or <2>, wherein at least some of the pits have a depth that is more than a half of the average thickness of the noble metal vapor-deposited film, <4> the biopolymer crystallization substrate according to any one of <1> to <3>, wherein at least some of the pits have a depth that exposes the substrate, <5> the biopolymer crystallization substrate according to any one of <1> to <4>, wherein the substrate with the noble metal vapor-deposited film formed on the substrate surface is a planar substrate, or a planar substrate with one or more wells formed in at least part of the substrate, <6> the biopolymer crystallization substrate according to any one of <1> to <5>, wherein the noble metal is gold, silver, platinum, and/or an alloy of these, <7> the biopolymer crystallization substrate according to any one of <1> to <6>, wherein the noble metal is gold, <8> the biopolymer crystallization substrate according to any one of <1> to <7>, wherein the noble metal vapor-deposited film has an average thickness of 5 to 50 nm, <9> the biopolymer crystallization substrate according to any one of <1> to <8>, wherein the substrate is for photo-irradiation crystallization of a biopolymer, <10> the biopolymer crystallization substrate according to any one of <1> to <9>, wherein the substrate is a substrate with a well, <11> the biopolymer crystallization substrate according to any one of <1> to <10>, wherein the substrate is a substrate with wells, and at least some of the wells have the noble metal vapor-deposited film, <12> the biopolymer crystallization substrate according to any one of <1> to <11>, wherein the noble metal vapor-deposited film has an absorption in the whole 500 to 1,000 nm wavelength range, <13> a biopolymer crystallization container comprising the biopolymer crystallization substrate of any one of <1> to <12>, <14> a biopolymer crystallization device comprising the biopolymer crystallization substrate of any one of <1> to <12>, <15> the biopolymer crystallization device according to <14>, wherein the device comprises photo-irradiation means that irradiates the noble metal vapor-deposited film with light, <16> a biopolymer crystal producing method comprising:
a preparation step of vapor depositing noble metal on all or part of one surface of a substrate to prepare the biopolymer crystallization substrate of any one of <1> to <12>; and
a contact step of contacting the noble metal vapor-deposited film to a biopolymer solution, <17> the biopolymer crystal producing method according to <16>, further comprising a photo-irradiation step of photo-irradiating the noble metal vapor-deposited film in contact with the biopolymer solution, <18> a crystallization substrate comprising a noble metal vapor-deposited film having an absorbance in a 500 to 1,000 nm wavelength range and formed on a substrate surface, <19> the crystallization substrate according to <18>, wherein the noble metal vapor-deposited film having an absorbance in a 500 to 1,000 nm wavelength range is formed in all or part of one surface of the substrate, wherein the noble metal vapor-deposited film has an average thickness of 0.1 to 60 nm, and wherein the noble metal vapor-deposited film is a continuous film with a pit formed by vapor deposition in part of the film and surrounded by the continuous film, <20> a crystallization container comprising the crystallization substrate of <18> or <19>, <21> a crystallization device comprising the crystallization substrate of <18> or <19>, <22> a crystal producing method comprising: a preparation step of preparing the crystallization substrate of <18> or <19>; and a contact step of contacting the noble metal vapor-deposited film to a crystallization material solution.

MODE FOR CARRYING OUT THE INVENTION

Figure 1:
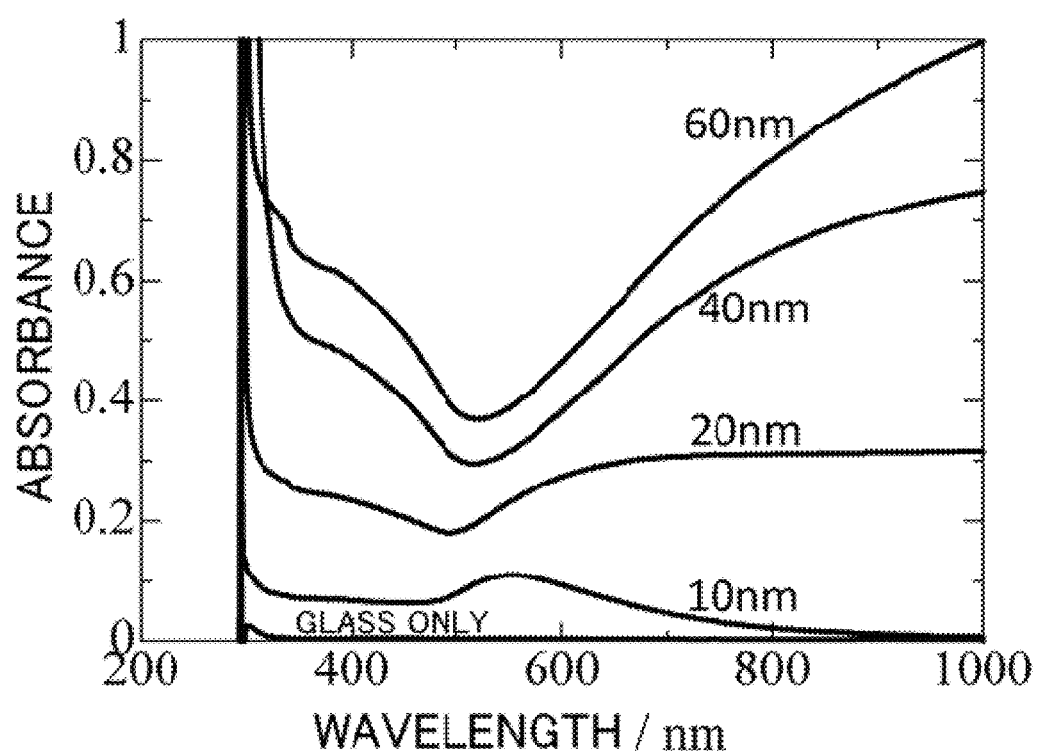
FIG. 1 is a diagram representing the absorption spectra of the gold thin films of Examples 1 to 4 and Comparative Example 1 in the 200 to 1,000 nm wavelength range.

The present invention is described below in detail.

In the present invention, the notation 'lower limit to upper limit' expressing a numerical range means 'at least the lower limit but no greater than the upper limit', and the notation 'upper limit to lower limit' means 'no greater than the upper limit but at least the lower limit'. That is, they are numerical ranges that include the upper limit and the lower limit.

Further, a combination of two or more preferred embodiments also represents a preferred form of the present invention.

Crystallization Substrate

The crystallization substrate of the present invention includes a noble metal film having an absorption in the 500 to 1,000 nm wavelength range and formed on a surface of the crystallization substrate.

The crystallization substrate of the present invention can preferably be used as a biopolymer crystallization substrate.

With the noble metal film having an absorption in the 500 to 1,000 nm wavelength range and formed on a surface of the crystallization substrate, the crystallization substrate of the present invention can conveniently and efficiently produce crystals, preferably biopolymer crystals.

The crystallization substrate of the present invention is preferably a biopolymer crystallization substrate that includes a noble metal vapor-deposited film having an absorption in the 500 to 1,000 nm wavelength range and formed on all or part of one surface of the substrate, the noble metal vapor-deposited film being provided as a continuous film with an average thickness of 0.1 to 60 nm, and having pits formed by vapor deposition in part of the film and surrounded by the continuous film.

Patent Document 4 discloses a technique that takes advantage of a gold periodic nanostructure to promote protein crystal formation. This method uses an electron beam lithography device to create a gold nanostructure, and takes about 20 hours to create 1 mm² of a periodic gold nanostructure in actual practice. Constructing such a gold nanostructure on a practical crystallization plate is practically impossible because it would take, for example, some 2,000 hours to fabricate even a single 96-well plate.

In contrast, the present invention uses a vapor deposition device to form a noble metal film, and the fabrication quickly completes in only about 5 minutes, making it possible to mass produce the film. Indeed, the present invention can be said as a more practical method than the invention described in Patent Document 4.

In the crystallization substrate of the present invention, the noble metal film having an absorption in the 500 to 1,000 nm wavelength range may be provided in at least a part of a substrate surface. For example, the noble metal film may be provided on all or part of one surface of the substrate, or on the both surfaces or side surfaces of the substrate.

However, for cost considerations, the noble metal film is preferably provided on all or part of one surface of the substrate.

The crystallization substrate of the present invention may preferably be used as a photo-irradiation crystallization substrate, more preferably a photo-irradiation biopolymer crystallization substrate.

The preferred photo-irradiation conditions are as described below in the preferred embodiment of the crystal producing method.

The shape of the crystallization substrate of the present invention is not particularly limited, and may be planar or non-planar. Other than the planar shape, the substrate may have any desired shape, including, for example, a polygonal column, a cylindrical column, a pyramid, a cone, a particle, and some other irregular shape. It is preferable, however, that the substrate is a planar substrate, or a planar substrate with one or more wells (depressions) formed in at least part of the substrate.

The crystallization substrate of the present invention preferably includes one or more wells in at least part of the substrate.

Figure 6:
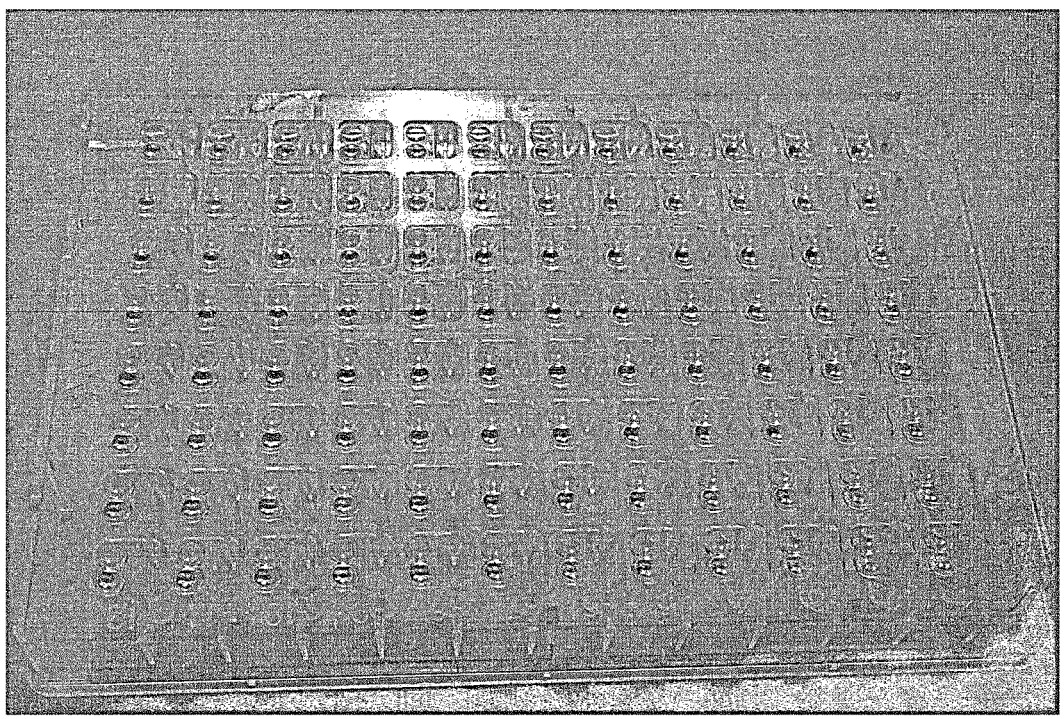
FIG. 6 represents an example of a crystallization substrate with wells.

FIG. 6 represents an example of a crystallization substrate with wells.

The substrate shown in FIG. 6 has a total of 96 (12×8) crystallization sites. The crystallization sites each have a structure with two mortar-like depressions joined to each other, and a noble metal film that has an absorption in the 500 to 1,000 nm wavelength range is formed at the bottom portion of one of the two depressions. The substrate can turn itself into a crystallization container upon installing a plate-like member at the top, as will be described later.

The size of the crystallization substrate of the present invention is not particularly limited, and the substrate may have any desired size.

The material of the crystallization substrate of the present invention is not particularly limited, as long as it is not noble metal. Examples include glass, resin, and metal. From the standpoint of crystal formation, the substrate material is preferably transparent material, particularly preferably glass.

Preferred examples of the transparent material include glass, and transparent resin.

The method used to measure the absorption spectrum of the noble metal film in crystallization substrate of the present invention is not particularly limited, and known methods may be used. Preferably, the spectrophotometer U-2010 or U-2100 (Hitachi High-Technologies) is used for the measurement.

The absorbance of the noble metal film of the crystallization substrate of the present invention at 600 nm wavelength is preferably 0.08 to 0.5, more preferably 0.08 to 0.45, yet more preferably 0.20 to 0.45. These ranges are preferred for crystal formation.

The average thickness of the noble metal film of the crystallization substrate of the present invention is preferably 0.1 to 60 nm, more preferably 5 to 50 nm, yet more preferably 10 to 50 nm, particularly preferably 15 to 45 nm. These ranges are preferred for crystal formation.

The average thickness of the noble metal film may be measured by using methods, for example, such as a method that calculates average thickness from the area of the noble metal film formed on the substrate, and the amount of the noble metal present on the substrate, and a method that calculates thickness by image processing of the substrate surface observed with an atomic force microscope (AFM) or a scanning electron microscope (SEM).

The average thickness of the noble metal film does not necessarily represent the average thickness of the noble metal film over the whole substrate, and may be the average thickness of the noble metal film in portions of the substrate where the noble metal film is formed.

The noble metal film in the crystallization substrate of the present invention preferably has a pit in part of the film. The pit improves the ease of crystal formation, possibly because of its involvement in the absorption spectrum of the noble metal film.

The noble metal film is preferably a vapor-deposited film of noble metal. With this embodiment, the pit can be more easily formed, and ease of crystal formation further improves.

The noble metal film is preferably a continuous film with a pit formed in part of the film and surrounded by the continuous film. More preferably, the noble metal film is a continuous film with a pit formed by vapor deposition in part of the film and surrounded by the continuous film. With this embodiment, ease of crystal formation further improves, and fabrication of the crystallization substrate becomes easier, possibly because of its involvement in the absorption spectrum of the noble metal film.

Preferred as the method of forming such a partially depressed noble metal film is, for example, a method in which noble metal is vapor deposited in at least a part of a substrate surface. Preferably, the noble metal film has an average thickness of 0.1 to 60 nm, because it makes it easier to form the partially depressed noble metal film by vapor deposition.

It is preferable that at least some of the pits in the noble metal film of the crystallization substrate of the present invention have a depth that is more than a half of the average thickness of the noble metal vapor-deposited film. Ease of crystal formation further improves with this embodiment, possibly because of its involvement in the absorption spectrum of the noble metal film.

It is preferable that at least some of the pits in the noble metal film of the crystallization substrate of the present invention expose the substrate. Ease of crystal formation further improves with this embodiment, possibly because of its involvement in the absorption spectrum of the noble metal film.

The size of the pit (a circle equivalent diameter of the aperture portion) is not particularly limited, and is preferably 10 nm to 20 μm, more preferably 100 nm to 10 μm, further preferably 200 nm to 10 μm, particularly preferably 200 nm to 5 μm in at least some of the pits. Ease of crystal formation further improves with this embodiment, possibly because of its involvement in the absorption spectrum of the noble metal film.

The method used to check the structure (including pits, and substrate exposure) of the noble metal film is not particularly limited, and, for example, methods such as atomic force microscopy (AFM), and scanning electron microscopy (SEM) may preferably be used.

It is preferable that the partially depressed noble metal film is formed by forming a noble metal film of 0.1 to 60 nm thickness by vapor deposition. The partially depressed film can easily be formed by forming a noble metal film of 0.1 to 60 nm thickness on the substrate. The noble metal film formed by vapor deposition is preferably a film that is not annealed (no heat treatment). Annealing appears to produce a noble metal vapor-deposited film of more uniform thickness.

The noble metal film in the crystallization substrate of the present invention is preferably a noble metal vapor-deposited film having a thickness of 0.1 to 60 nm, more preferably an unannealed noble metal vapor-deposited film having a thickness of 0.1 to 60 nm. Ease of crystal formation further improves with this embodiment, possibly because of its involvement in the absorption spectrum of the noble metal film.

The noble metal forming the noble metal film in the crystallization substrate of the present invention is preferably gold, silver, platinum, and/or an alloy of these, more preferably gold, silver, or platinum, particularly preferably gold. Ease of crystal formation further improves with this embodiment.

The materials crystallized with the crystallization substrate of the present invention are not particularly limited, and may be inorganic compounds, organic compounds, or polymer compounds, preferably biopolymers. For example, when the crystallization substrate of the present invention is used to crystallize a biopolymer, it is preferable to induce crystallization without irradiation with a strong laser beam or UV rays, because irradiation to a biopolymer solution with such a strong laser beam or UV rays as in the methods described in Patent Document 1 to 3 has the possibility of denaturing the biopolymer.

Specific examples of the biopolymers include polypeptides, proteins, nucleic acids (for example, DNA), and derivatives thereof. The biopolymers also include synthetic products such as synthetic polypeptides, and synthetic proteins. The polypeptides may be, for example, polypeptides expressed in *Escherichia coli*, yeasts, and animal cells, and isolated by using common methods, or synthetic polypeptides. The derivatives of polypeptides, proteins, nucleic acids include, for example, sugar proteins, and DNA conjugates.

The (weight average) molecular weight of the biopolymer is preferably 1,000 or more, more preferably 1,000 to 1 million. Preferred as the biopolymer are polypeptides, proteins, and derivatives thereof, more preferably proteins and their derivatives (also referred to simply as "proteins" in the present invention). The proteins are inclusive of enzymes.

Crystallization Container

The crystallization container of the present invention is a crystallization container that includes the crystallization substrate of the present invention.

In the crystallization container of the present invention, the container itself and the crystallization substrate of the present invention may be physically or chemically bonded to each other, or may not be bonded to each other. Specifically, for example, the crystallization substrate of the present invention may be bonded inside the crystallization container of the present invention, or the crystallization substrate of the present invention may be simply placed in the container.

The crystallization container of the present invention may include only one crystallization substrate of the present invention, or two or more crystallization substrates of the present invention.

The crystallization container of the present invention is not limited to a particular shape, and may have any desired shape, as long as the noble metal film of the crystallization substrate of the present invention can be brought in contact with a solution containing the material to be crystallized.

The crystallization container of the present invention is preferably a sealable container so that evaporation of the crystallization material solution can be suppressed during the crystallization process.

The crystallization container of the present invention is preferably at least partially transparent for ease of photo-irradiation.

The size of the crystallization container of the present invention is not particularly limited, and may be appropriately decided according to needs.

Preferred specific examples of the crystallization container of the present invention include a container in which the crystallization substrate of the present invention with one or more wells formed in at least part of the substrate is combined with a well sealable member, or a container that can install and seal the crystallization substrate of the present invention inside the container.

Crystal Producing Method

The crystal producing method of the present invention includes a preparation step of preparing the crystallization substrate of the present invention, and a contact step of contacting the noble metal film to a crystallization material solution.

The crystal producing method of the present invention is preferably used as a biopolymer crystal producing method. The crystallization material solution is preferably a biopolymer solution.

From the standpoint of further promoting crystal formation, the crystal producing method of the present invention preferably further includes a step of photo-irradiating the noble metal film in contact with the crystallization material solution (hereinafter, also referred to as "photo-irradiation step").

The crystal producing method of the present invention preferably further includes a step of storing the crystallization material solution after the contact step or the photo-irradiation step (hereinafter, also referred to as "storage step").

Preparation Step

The crystal producing method of the present invention includes the preparation step of preparing the crystallization substrate of the present invention.

The method used to form the noble metal film of the crystallization substrate of the present invention is not particularly limited, and a known method may be used, and the noble metal film is preferably formed in at least part of the substrate by vapor deposition, and is more preferably formed in at least part of the substrate by vapor deposition, and the vapor deposition is not followed by annealing.

Specifically, the preparation step is preferably a step that vapor deposits noble metal on the substrate, and in which annealing is not performed during and after the preparation step before the contact step.

Contact Step

The crystal producing method of the present invention includes the contact step of contacting the noble metal film of the crystallization substrate of the present invention to a crystallization material solution.

The contact step is not particularly limited, as long as the noble metal film of the crystallization substrate of the present invention is contacted to a crystallization material solution.

The crystallization material solution may be a solution that contains a crystallization material, and a solvent for dissolving the crystallization material, and the crystallization material solution is preferably a solution in which the crystallization material is completely dissolved.

The solvent used for the crystallization material solution may be independently selected according to the crystallization material used, and may be, for example, water, an organic solvent, or a mixture of water with an organic solvent in water (aqueous organic solvent).

When the crystallization material is a biopolymer, the solvent is preferably a buffer, more preferably an acetate buffer, a CAPS buffer, a HEPES buffer, a citrate buffer, a tartrate buffer, a carcodylate buffer, or a Tris buffer. When using an ampholyte biopolymer, it is preferable to photo-irradiate the biopolymer solution after adjusting the solution pH near the isoelectric point of the biopolymer, or prepare a mixture of such a solution with the adjusted pH.

The concentration of the crystallization material in the crystallization material solution is not particularly limited, and the solution may be, for example, a solution with 1 to 100% of saturation concentration, or a supersaturated solution. The concentration is preferably 80% or more, preferably 90% or more of saturation concentration, particularly preferably a saturation concentration or supersaturated.

In order to maintain the solution concentration, for example, the solution may be supplemented with the crystallization material, which is a solute, or the temperature of the solution may be lowered, and/or a precipitant may be added.

The crystallization material solution of the present invention may contain a crystallizing agent.

As used herein, "crystallizing agent" means a compound that acts to lower the solubility of the crystallization material, preferably a biopolymer, and may be, for example, a precipitant, a pH buffer, and other additives used for crystallization of polymers.

Examples of the crystallizing agent usable in the present invention include salts, organic solvents, and water-soluble polymers, and known crystallizing agents may be used. The crystallizing agent may be appropriately selected according to the crystallization material used.

Examples of the salts include sulfates, nitrates, phosphates, organic acid salts, and alkali metal or alkali earth metal halides. Specific examples include ammonium sulfate, sodium chloride, and sodium citrate.

Examples of the organic solvents include water-soluble organic solvents, and specific example of the organic solvents include 2-methyl-2,4-pentadiol (MPD), ethanol, and propanoldioxane.

Examples of the water-soluble polymers include polyethylene glycol, and polypropylene glycol.

The amount of the crystallizing agent added is not particularly limited, and may be appropriately decided according to the types of the crystallization material and the crystallizing agent used.

For ease of crystal production, the biopolymer used in the present invention preferably has high purity and high homogeneity. To this end, the biopolymer crystal producing method of the present invention preferably includes a step of purifying the biopolymer in advance of crystal production.

The purification of the biopolymer before crystallization may be performed by using a known method, preferably, for example, such as affinity chromatography, common chromatography, rpHPLC, and FPLC.

For the production of nucleic acid crystals, it is preferable to crystallize nucleic acids after increasing the purity of the nucleic acids isolated by using a known isolation method.

For proteins, it is preferable to perform crystallization after increasing purity by using a known method, and confirming the purity by using methods such as isoelectric focusing electrophoresis, and a light scattering method.

In addition to the crystallization material, the solvent, and the crystallizing agent, other known additives may be added to the crystallization material solution, as required. As is evident, care should be taken that such addition does not interfere with the crystallization in the storage step (described later).

The additives may be added at once, or in separate portions.

Photo-Irradiation Step

The crystal producing method of the present invention preferably further includes the photo-irradiation step of photo-irradiating the noble metal film in contact with a crystallization material solution.

As used herein, "photo" referring to light may be an electromagnetic wave such as ultraviolet light, visible light, and infrared light.

The wavelength of the irradiation light in the photo-irradiation step is not particularly limited, and is preferably longer than 400 nm, more preferably 450 to 2,000 nm, yet more preferably 500 to 1,500 nm, particularly preferably 500 to 1,200 nm.

The irradiation light in the photo-irradiation step preferably includes at least visible light and/or near-infrared light, and more preferably includes only visible light and/or near-infrared light.

In the present invention, the visible light is preferably of 400 nm to 780 nm wavelengths.

In the present invention, the near-infrared light is preferably of wavelengths in more than 780 nm and no greater than 2,500 nm, more preferably wavelengths in more than 780 nm and no greater than 2,000 nm.

The irradiation light in the photo-irradiation step may be monochromatic light, or continuous light.

The intensity of the photo-irradiation may be appropriately selected, and, typically, light having a power of several microwatts to a few hundred watts may be used.

The photo-irradiation may be constant or pulsed. The irradiation intensity, the energy per pulse, the pulse interval, and other parameters may be varied, as required.

The photo-irradiation of constant light is preferably continuously performed, though the irradiation may be intermittent or paused.

The photo-irradiation time in the photo-irradiation step is not particularly limited, and the photo-irradiation may be performed either continuously or intermittently until crystals are formed.

Storage Step

The crystal producing method of the present invention preferably further includes the storage step of storing the crystallization material solution after the contact step or the photo-irradiation step.

The storage step may be simultaneously performed with the photo-irradiation step. For example, the crystallization material solution may be allowed to stand under light to form crystals.

Storage time may be appropriately selected under the conditions that crystallization material growth sufficiently takes place. For example, storage time may be appropriately decided taking into consideration factors such as the types of the crystallization material, the crystallizing agent, and the solvent used, the presence or absence of crystal formation, and the size of the generated crystals.

Storage temperature is not particularly limited, as long as it does not interfere with the crystallization of the crystallization material. Storage temperature may be constant or varied. Temperature changes are preferably within 1° C.

The crystallization material solution in the storage step may be stored in a sealed container or in a non-sealed container. Inside and outside the container, the solvent amount in the atmosphere, for example, humidity may be appropriately set, as required. The atmosphere inside and outside the container may be appropriately selected according to the type of the crystallization material used, and may be, for example, an air atmosphere, a nitrogen or argon atmosphere.

In the storage step, the solution may be allowed to stand or may be agitated, or may be continuously, intermittently, or temporarily vibrated. Large grain crystals may be obtained by agitating and/or vibrating the solution during the storage.

The frequency of the agitation in the storage step is preferably 10 rpm to 300 rpm, more preferably 20 rpm to 100 rpm, yet more preferably 30 rpm to 60 rpm.

Determination Step

The crystal producing method of the present invention preferably further includes the determination step of determining the presence or absence of generated crystals in the solution.

The method used to determine the presence or absence of crystals in the determination step is not particularly limited, and may be, for example, observation by visual inspection, or image processing or optical techniques using sensors.

The determination step is preferably performed on a regular basis, as required. For example, the determination step may be performed on day 1, 2, 3, 5, 7, 30, 60, and 90 of the storage period.

When crystals are determined as being absent in the solution, the solution with no crystals may be subjected to the photo-irradiation step again. Alternatively, the photo-irradiation step and the storage step may be repeated multiple times until crystals generate, as required.

In the crystal producing method of the present invention, the generated crystals in the solution may be separated by using any method. Specifically, for example, the crystals may be separated by filtration with a filter paper or a filter, or may be collected with tweezers or the like.

The resulting crystals may be washed, dried, processed into the desired size and shape, or recrystallized, as required.

The form of crystallization in the crystal producing method of the present invention is not particularly limited, and crystallization may be performed by using known techniques. For biopolymer crystallization, techniques, for example, such as hanging drop vapor diffusion, sitting drop vapor diffusion, microdialysis, free interface diffusion, and the storage batch technique may preferably be used.

Other conditions for promoting biopolymer crystallization can be found in Shin Seikagaku Jikken Koza 1, ed., The Japanese Biochemical Society, Protein I—Separation, Purification, and Property—, 1990, Tokyo Kagaku Dojin, Tsunehiro Takano, Chapter 14, Crystallization, and in A. McPherson, Preparation and Analysis of Protein Crystals (John Wiley & Son, Inc.).

The devices used for the crystal producing method of the present invention are not particularly limited, and known means and devices may be used in combination.

The device used for the crystal producing method of the present invention preferably includes photo-irradiation means that irradiates the noble metal film with light, and may optionally include other means, for example, such as solution preparing means, temperature adjusting means, humidity adjusting means, agitation means, vibration means, storage means, crystal presence or absence determining means, and additive adding means, as required.

Further, two or more devices with at least one essential means may be used in combination for the crystal producing method of the present invention, or a single device equipped with all the necessary means may be used.

The vibration means may be, for example, a known vibration, agitation, or ultrasonic generating means.

The vibrator of the vibration means may be of various configurations such as a piezoelectric vibrator, a suction force, or magnetic force, and is not particularly limited as long as it can produce vibration.

The biopolymer solution may be vibrated, for example, by using a method in which a container with the biopolymer solution is contacted to a vibrating vibration means, or a method in which a container with the biopolymer solution is anchored to a plate, and vibrated through the whole plate.

The photo-irradiation means may be realized by, for example, a light source, and an optical system that guides light to the solution. The optical system preferably includes optical parts such as lenses and mirrors that efficiently transmit or reflect light, for example, such as those commonly used in a light path from a light source to an irradiation sample.

A constant light source or a laser light source, such as those exemplified above, can be preferably used as a light source.

The optical system may use optical members such as a reflecting mirror, a condensing lens, a light filter, an infrared cutoff filter, an optical fiber, a light guide plate, and a nonlinear optical element, as appropriate.

Examples of the temperature adjusting means include known heating means, cooling means, and combinations of such means. Temperature may be detected by detecting the inner temperature of the biopolymer solution or mixture, or by detecting the ambient outside air temperature. The temperature adjusting means may include a program circuit that performs the necessary temperature adjustments.

The storage means is not particularly limited, as long as it allows for the storage of, for example, the noble metal film in contact with the biopolymer solution. Preferably, the storage means is one that allows the contacting noble metal film and biopolymer solution to stand, more preferably one that allows the contacting noble metal film and biopolymer solution to stand in a sealed space.

The device used for the crystal producing method of the present invention may optionally include devices, circuits, and programs for detecting and controlling parameters such as generation of a crystal nucleus in the solution, and solution pH, as required. Preferably, the device used for the detection and control of crystallization conditions is one that has integrated a plurality of crystallization condition detection cells into a single chip. Such a detection chip may be produced according to common semiconductor device manufacturing processes, for example, such as the process described in JP-A-2001-213699.

The device used for the crystal producing method of the present invention, particularly the biopolymer crystal producing method may include a means by which a laser beam of a long wavelength not absorbed by a biopolymer and having no contribution to crystal nucleus generation or crystal growth is used for the detection of crystal nucleus generation, such as that described in JP-A-6-116098.

The biopolymer crystals obtained by using the crystal producing method of the present invention have use as an X-ray crystalline structure analysis sample. Further, the very high storage stability commonly seen in the biopolymer crystals allows the crystals to be used as pharmaceutical compositions of preventive or therapeutic formulation. Because the biopolymer is in the form of crystals, various advantageous administrations are possible. The biopolymer crystals are suitable for, for example, oral, subcutaneous, intradermal, intraperitoneal, intravenous, and intramuscular administrations. The biopolymer crystals obtained by using the crystal producing method of the present invention may preferably be used as an active substance of a pharmaceutical composition containing the crystallized biopolymer in pharmaceutically effective amounts, and one or more common pharmaceutically acceptable carriers, as required.

The biopolymer crystals obtained by using the crystal producing method of the present invention may also be used, in principle, as a depot preparation for administering a pharmaceutical preparation, for example, in a daily dose of 0.001 μg/kg to 100 mg/kg body weight in terms of a pharmaceutically effective biopolymer, by using methods available for many types of biopolymers. The present invention thus enables using a wide range of biopolymers, for example, as therapeutic agent depot preparations, antigen depot preparations, DNA depot preparations, or sugar depot preparations in the form of crystals produced according to the present invention. The crystallization inducing agent contained in the crystals can also be used as an adjuvant (in vaccinations).

Crystallization Device

The crystallization device of the present invention is a crystallization device that includes the crystallization substrate of the present invention.

The crystallization device of the present invention is preferably used for the crystal producing method of the present invention.

The crystallization device of the present invention may include one or more of the crystallization substrate of the present invention.

The crystallization device of the present invention may include the crystallization substrate of the present invention as the crystallization container of the present invention.

The shape of the crystallization device of the present invention is not particularly limited, and the crystallization device may have any desired shape, as long as the noble metal film of the crystallization substrate of the present invention and the crystallization solution can be brought into contact with each other.

The crystallization device of the present invention is preferably sealable in a portion provided with the crystallization substrate of the present invention, so that evaporation of the solution containing the crystallization material can be suppressed during the crystallization process.

The crystallization device of the present invention preferably includes photo-irradiation means that irradiates the noble metal film of the crystallization substrate of the present invention with light.

The device used for the crystal producing method of the present invention may include other means, for example, such as solution preparing means, storage means, temperature adjusting means, humidity adjusting means, agitation means, vibration means, crystal presence or absence determining means, and additive adding means, as required.

Preferred examples of each of these means include means as described above in conjunction with the crystal producing method.

Further, two or more devices with at least one essential means may be used in combination for the crystal producing method of the present invention, or a single device equipped with all the necessary means may be used.

The present invention has thus enabled providing a crystallization substrate, a crystallization container, a crystallization device, and a crystal producing method with which crystals, preferably biopolymer crystals can be conveniently and efficiently produced.

EXAMPLES

The present invention is described below using Examples. The present invention is not limited by the following Examples.

Example 1

Substrate Fabrication

A gold thin film (average thickness 40 nm) was vapor deposited on one surface of cover glass (diameter 22 mm, thickness 0.2 mm) under 99.99% gold purity and $10^{-1}$ Pa vacuum conditions, using an ion sputtering device JFC-1500 (vapor deposition device available from JEOL).

Atomic force microscopy (S-weep spi3800; Seiko Instruments Inc.) of the cover glass revealed the presence of pits in the gold thin film of the cover glass.

The absorption spectrum of the gold thin film on the cover glass was measured with a spectrophotometer U-2100 (Hitachi High-Technologies). The gold thin film had an absorption in the whole 500 to 1,000 nm wavelength range. The absorbance at 600 nm wavelength was 0.38.

Crystallization of Biopolymer

A 50 mM sodium acetate buffer solution with a pH 4.3 containing 15 mg/mL of chicken egg white lysozyme, and 0.7 M sodium chloride was used as a protein solution.

10 μl of the protein solution was dropped onto the cover glass in a manner allowing the solution to contact the gold thin film, and the cover glass was placed in a batch plate (96-well vapor diffusion batch plate DI-038; Hampton Research). A reservoir solution containing the same concentration of sodium chloride as in the dropped protein solution was dropped around the cover glass inside the batch plate, and the batch plate was lidded to prevent evaporation of the protein solution.

A xenon lamp (300 W xenon lamp; Ushio Inc.) was used for photo-irradiation. For irradiation, the light from the xenon lamp was filtered through a water filter for infrared absorption, and through a 400 nm cut filter for UV absorption. The solution on the cover glass inside the batch plate was allowed to stand in a 20° C. incubator under the xenon lamp light.

The number of protein crystals that emerged from the solution was counted after 6, 12, and 24 hours from the start of the photo-irradiation.

Separately, the solution was allowed stand in a 20° C. incubator, and the number of protein crystals that emerged from the solution was counted after 6, 12, and 24 hours in the same manner as above, without photo-irradiation.

The crystals obtained were tetragonal crystals of the chicken egg white lysozyme.

The results are presented in Table 1.

Example 2

Substrate fabrication, and biopolymer crystallization were performed in the same manner as in Example 1, except that the gold thin film was vapor deposited to make the average thickness 20 nm. The results are presented in Table 1.

Atomic force microscopy of the cover glass revealed the presence of pits in the gold thin film of the cover glass.

The absorption spectrum of the gold thin film on the cover glass was measured with the spectrophotometer. The gold thin film had an absorption in the whole 500 to 1,000 nm wavelength range. The absorbance at 600 nm wavelength was 0.28.

Example 3

Substrate fabrication, and biopolymer crystallization were performed in the same manner as in Example 1, except that the gold thin film was vapor deposited to make the average thickness 10 nm. The results are presented in Table 1.

Atomic force microscopy of the cover glass revealed the presence of pits in the gold thin film of the cover glass.

The absorption spectrum of the gold thin film on the cover glass was measured with the spectrophotometer. The gold thin film had an absorption in the whole 500 to 1,000 nm wavelength range. The absorbance at 600 nm wavelength was 0.09. The absorbance at 1,000 nm wavelength was 0.005 or higher.

Example 4

Substrate fabrication, and biopolymer crystallization were performed in the same manner as in Example 1, except that the gold thin film was vapor deposited to make the average thickness 60 nm. The results are presented in Table 1.

Atomic force microscopy of the cover glass revealed the presence of pits in the gold thin film of the cover glass.

The absorption spectrum of the gold thin film on the cover glass was measured with the spectrophotometer. The gold thin film had an absorption in the whole 500 to 1,000 nm wavelength range. The absorbance at 600 nm wavelength was 0.46.

The number of crystals obtained upon photo-irradiation in Example 4 was smaller than in Examples 1 to 3. However, the crystals were larger in Example 4.

Comparative Example 1

Substrate fabrication, and biopolymer crystallization were performed in the same manner as in Example 1, except that the gold thin film was not vapor deposited. The results are presented in Table 1.

The absorption spectrum of the cover glass was measured with the spectrophotometer. There was no absorption in the whole 500 to 1,000 nm wavelength range.

Figure 2:
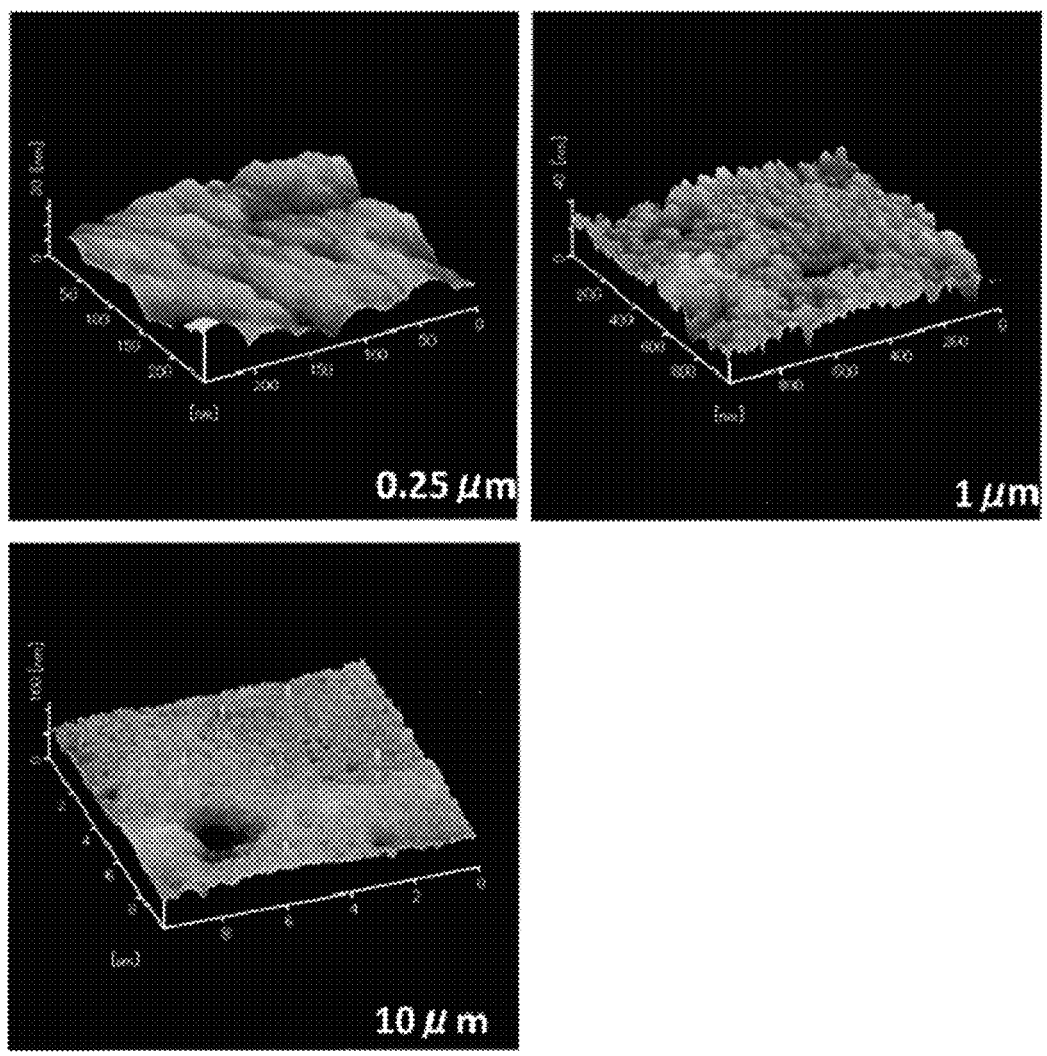
FIG. 2 shows atomic force micrographs of the gold thin film of Example 1 in three different magnifications.
Figure 3:
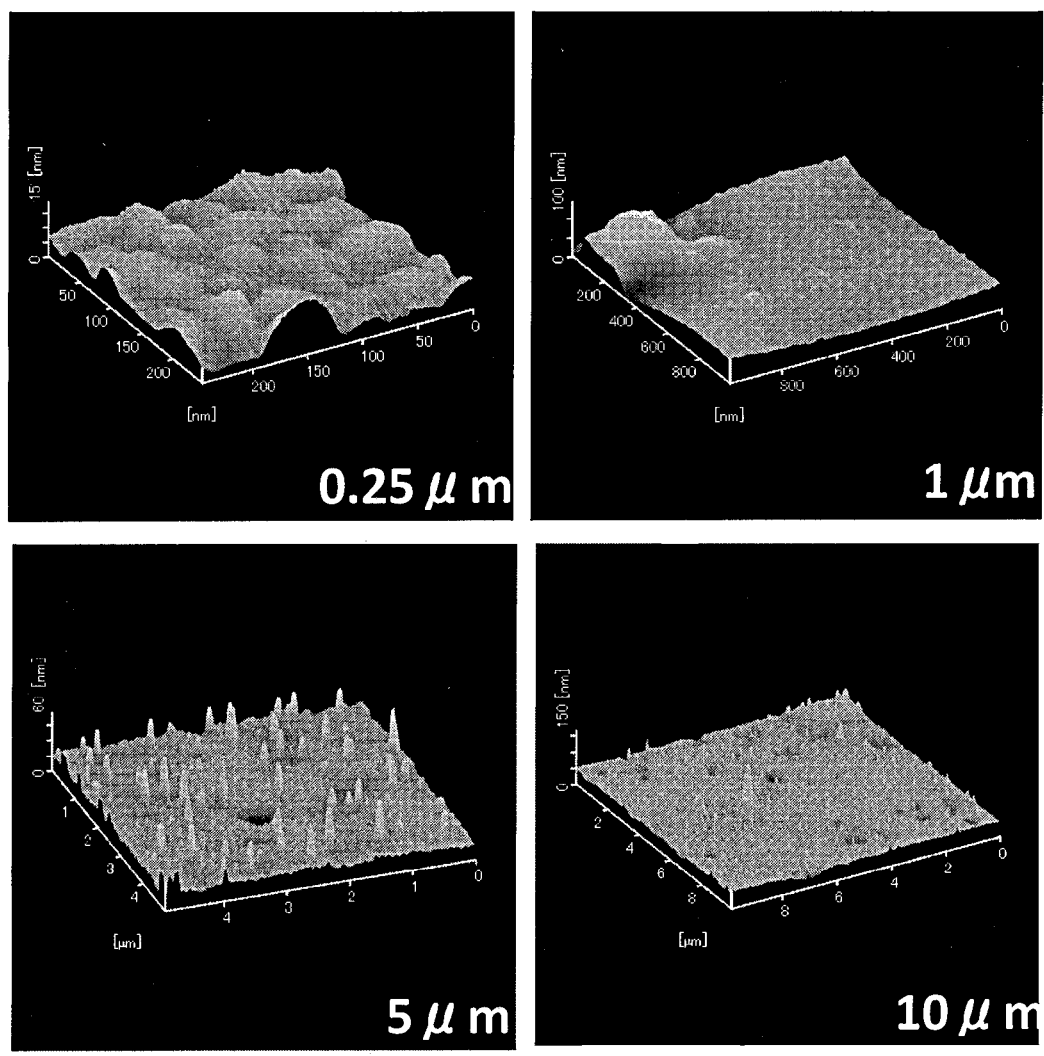
FIG. 3 shows atomic force micrographs of the gold thin film of Example 2 in four different magnifications.

FIG. 2 shows atomic force micrographs of the gold thin film of Example 1 in three different magnifications. FIG. 3 shows atomic force micrographs of the gold thin film of Example 2 in four different magnifications.

Example 5

Substrate fabrication, and biopolymer crystallization were performed in the same manner as in Example 2, except that the cover glass with the gold thin film (average thickness 20 nm) was annealed for 2.5 hours at 500° C. after raising the temperature to 500° C. from room temperature over the time period of 30 minutes.

Atomic force microscopy of the cover glass revealed that the gold thin film on the cover glass did not have pits that were 200 nm or greater in size and surrounded by the continuous gold thin film.

Figure 4:
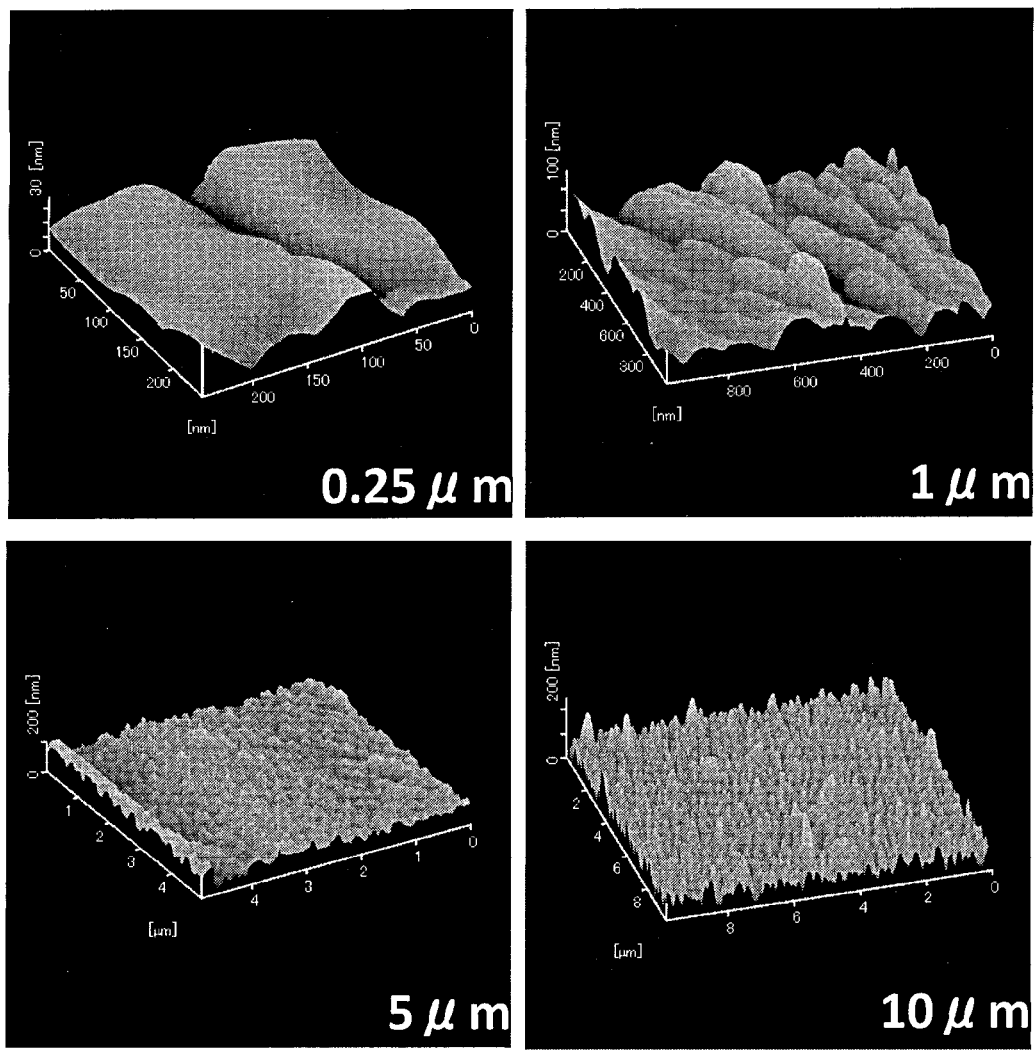
FIG. 4 shows atomic force micrographs of the gold thin film of Example 5 in four different magnifications.

FIG. 4 shows atomic force micrographs of the gold thin film of Example 5 in four different magnifications.

Figure 5:
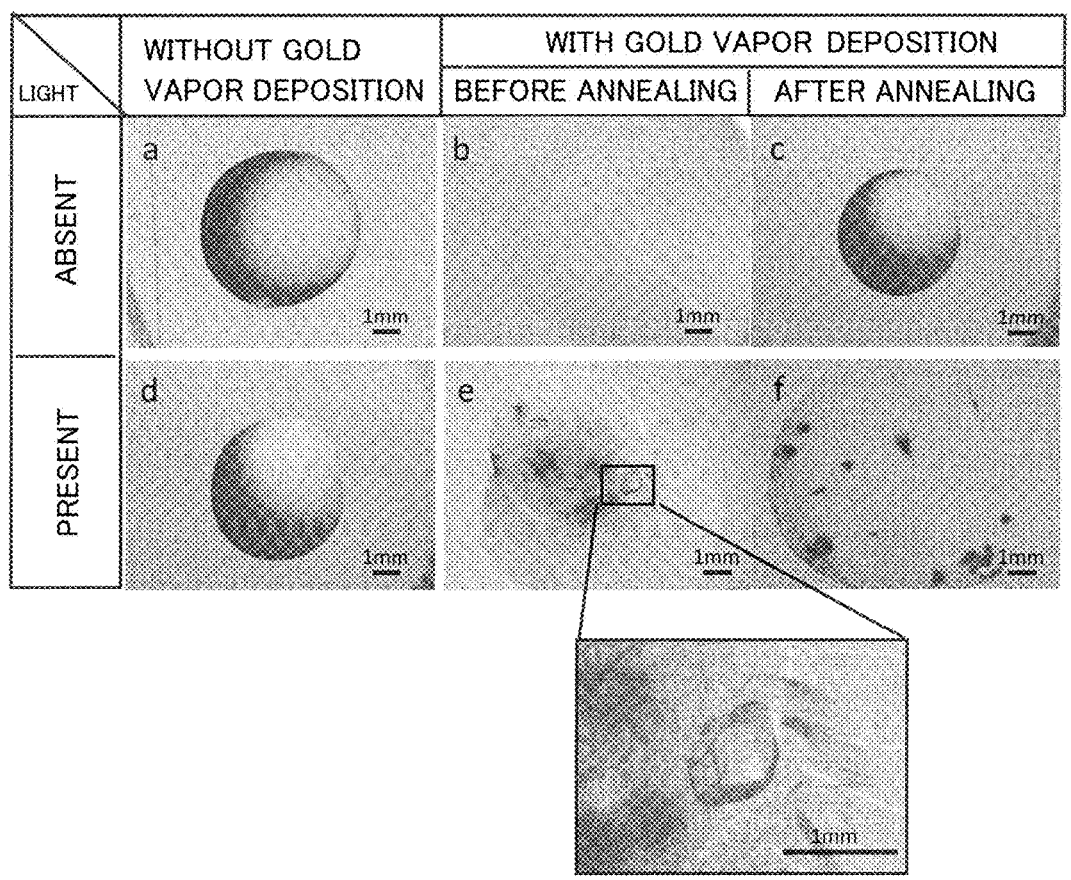
FIG. 5 shows the results for Example 2 (gold vapor deposition, before annealing), Example 5 (gold vapor deposition, after annealing), and Comparative Example 1 (no gold vapor deposition) after 24 hours.

FIG. 5 shows the results for Example 2 and Comparative Example 1 after 24 hours. The micrographs shown in FIG. 5 were taken with the stereomicroscope system SZX9, and the digital camera for microscopy DP25, both available from Olympus.

Tetragonal crystal formation from the chicken egg white lysozyme was confirmed for the cover glass of Example 5. However, the number of crystals was smaller than in Example 2.

Example 6

Figure 7:
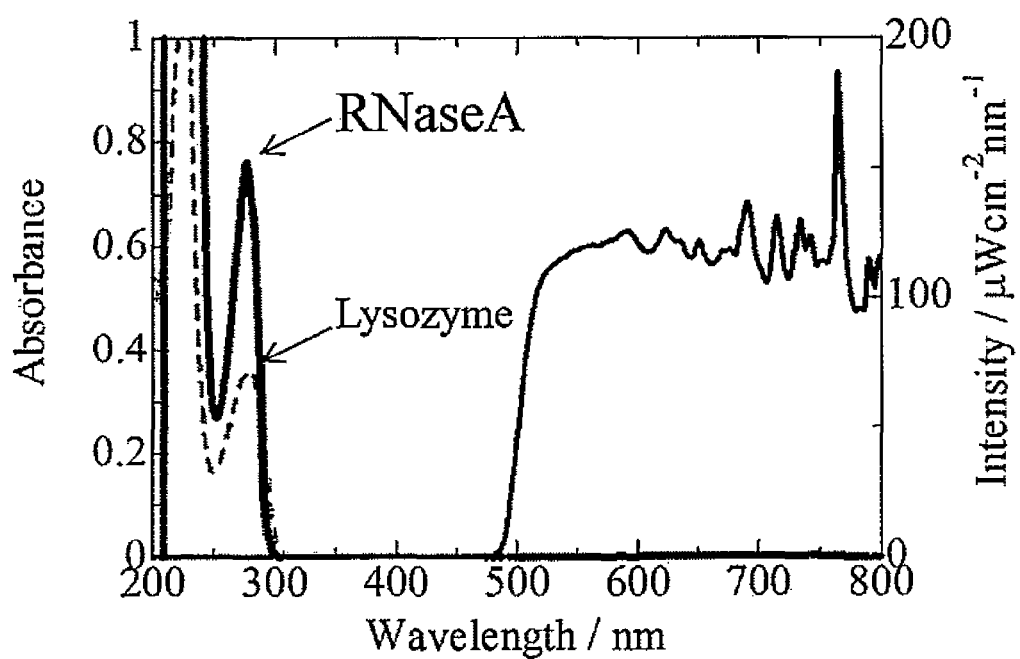
FIG. 7 represents an emittance spectrum of the light source used in Example 6, a ribonuclease A absorption spectrum, and an absorption spectrum of chicken egg white lysozyme.

Substrate fabrication, and biopolymer crystallization were performed in the same manner as in Examples 1 to 5, except that the chicken egg white lysozyme was replaced with ribonuclease A (RNase A). For the experiment, a 20° C. solution containing 17 mg/mL of RNase A, and crystallization reagents NaCl (2.2 M) and ammonium sulfate (1.39 M) was used. The solution under this condition corresponds to a concentration three times higher than the solubility, and is in a metastable state where crystallization does not take place spontaneously. FIG. 7 represents an emittance spec-

TABLE 1

| | | Number of generated biopolymer crystals | | | | | |
|---|---|---|---|---|---|---|---|
| | Average thickness of gold thin film | After 6 h Photo-irradiation | | After 12 h Photo-irradiation | | After 24 h Photo-irradiation | |
| | | Present | Absent | Present | Absent | Present | Absent |
| Comp. Ex. 1 | Absent | 0 | 0 | 0 | 0 | 0 | 0 |
| Ex. 3 | 10 nm | 42 | 0 | 42 | 0 | 49 | 3 |
| Ex. 2 | 20 nm | 17 | 0 | 19 | 0 | 33 | 0 |
| Ex. 1 | 40 nm | >40 | 4 | >80 | 4 | >150 | 12 |
| Ex. 4 | 60 nm | 1 | 0 | 1 | 0 | 1 | 0 |

In Table 1, the symbol ">" means greater than the numbers on the right.

FIG. 1 represents absorption spectra of the gold thin films of Examples 1 to 4 and Comparative Example 1 in the 200 to 1,000 nm wavelength range. In FIG. 1, the vertical axis represents absorbance, and the horizontal axis represents wavelength.

trum of the light source used for the photo-induced crystallization (FIG. 7; the line on the right), and an RNase A absorption spectrum (FIG. 7; thick line; vertical axis: Absorbance). The RNase A has an absorption on the wavelength side shorter than 300 nm, and has substantially the same spectrum shape as the absorption spectrum of the chicken egg white lysozyme (FIG. 7; dotted line; vertical axis: Absorbance). A xenon short arc lamp (UXL-300D; Ushio Inc.) was used as the light source in this Example, and the light was filtered through a sharp cut filter (SCF-50S-52Y; Sigma Koki) to obtain light longer than 520 nm wavelength. The spectrum of the filtered irradiation light on the RNase A solution is shown in FIG. 7 (the line on the right; vertical axis: Intensity). The light is on the longer wavelength side than the absorption wavelength of the RNase A, and is not absorbed by RNase A. A mortar-shaped acrylic resin container (depth of about 3 mm, the diameter of the bottom surface 1 mm) was used as the crystallization container in the crystallization experiment. The container had a 20 nm-thick gold thin film vapor deposited on the container surface. For comparison, gold was not vapor deposited in half of the containers used.

Figure 8:
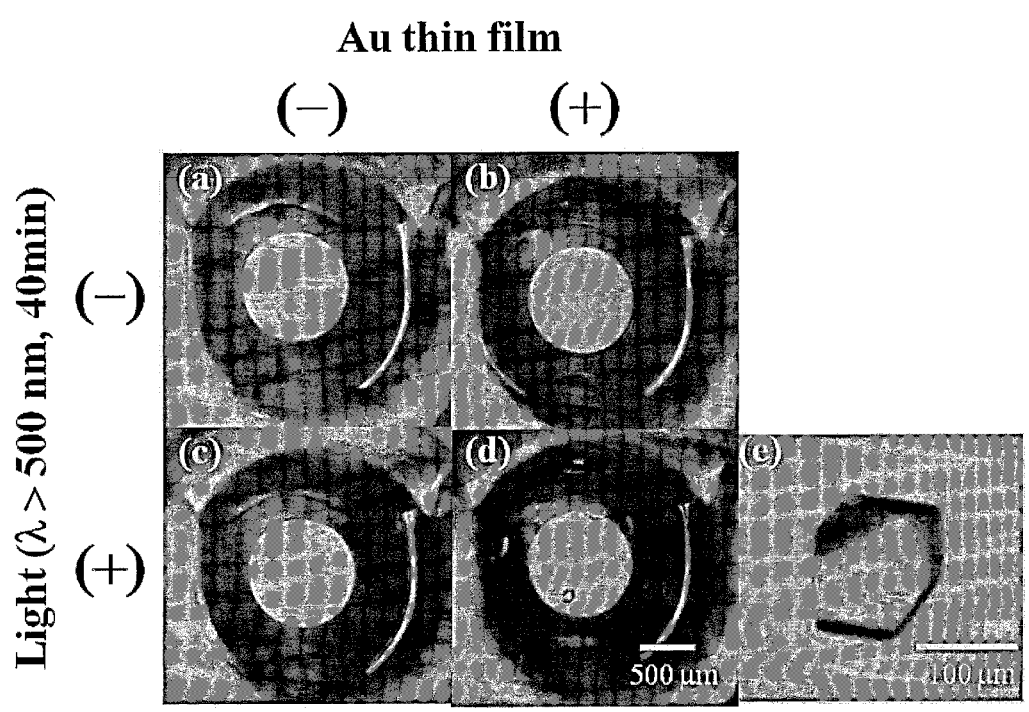
FIG. 8 represents the results of the crystallization experiment conducted in Example 6.

The results of the crystallization experiment are shown in FIG. 8. The portions with and without the gold vapor deposition (Au thin film) are represented by Au(+) and Au(−), respectively. The photo-irradiated portions are represented by Light(+) and Light(−). As shown in the results, several crystals emerged in Au(+) and Light(+) portions (FIG. 8(d)). FIG. 8(e) shows a magnified view of the crystal generated in Au(+)/Light(+). The crystal measured about 100 μm in size, and had the same shape as that previously reported. These results confirmed that crystallization was promoted also for the ribonuclease A (RNase A).

Example 7

Substrate fabrication, and biopolymer crystallization were performed in the same manner as in Examples 1 to 5, except that the chicken egg white lysozyme was replaced with thaumatin. Crystals were obtained in about the same numbers as those obtained in Examples 1 to 5.

The invention claimed is:
1. A biopolymer crystal producing method comprising:
   (a) a preparation step of vapor depositing noble metal on all or part of one surface of a biopolymer crystallization substrate to prepare a biopolymer crystallization substrate, wherein the biopolymer crystallization substrate comprises:
   a noble metal vapor-deposited film having an absorbance in a 500 to 1,000 nm wavelength range and formed in all or part of one surface of the biopolymer crystallization substrate,
   wherein the noble metal vapor-deposited film has an average thickness of 10 to 60 nm, and
   wherein the noble metal vapor-deposited film is a continuous film with pits formed by vapor deposition in part of the film and surrounded by the continuous film; and
   (b) a contact step of contacting the noble metal vapor-deposited film to a biopolymer solution.
2. The biopolymer crystal producing method according to claim 1, wherein the absorbance of the noble metal vapor-deposited film at 600 nm wavelength is 0.08 to 0.5.
3. The biopolymer crystal producing method according to claim 1, wherein at least some of the pits have a depth that is more than a half of the average thickness of the noble metal vapor-deposited film.
4. The biopolymer crystal producing method according to claim 1, wherein at least some of the pits have a depth that exposes the substrate.
5. The biopolymer crystal producing method according to claim 1, wherein the substrate with the noble metal vapor-deposited film formed on the substrate surface is a planar substrate, or a planar substrate with one or more wells formed in at least part of the substrate.
6. The biopolymer crystal producing method according to claim 1, wherein the noble metal is gold, silver, platinum, and/or an alloy of these.
7. The biopolymer crystal producing method according to claim 1, wherein the noble metal is gold.
8. The biopolymer crystal producing method according to claim 1, wherein the noble metal vapor-deposited film has an average thickness of 10 to 50 nm.
9. The biopolymer crystal producing method according to claim 1, wherein the substrate is for photo-irradiation crystallization of a biopolymer.
10. The biopolymer crystal producing method according to claim 1, wherein the substrate is a substrate with a well.
11. The biopolymer crystal producing method according to claim 1, wherein the substrate is a substrate with wells, and at least some of the wells have the noble metal vapor-deposited film.
12. The biopolymer crystal producing method according to claim 1, wherein the noble metal vapor-deposited film has an absorption in the whole 500 to 1,000 nm wavelength range.
13. The biopolymer crystal producing method according to claim 1, further comprising a photo-irradiation step of photo-irradiating the noble metal vapor-deposited film in contact with the biopolymer solution.

* * * * *